United States Patent [19]

Luczenbacher, Sr. et al.

[11] Patent Number: 5,313,665
[45] Date of Patent: May 24, 1994

[54] WELDER'S SHIELD, IN PARTICULAR FOR ARC WELDING

[76] Inventors: Janos Luczenbacher, Sr.; Janos Luczenbacher, Jr., both of Veresegyhaz u.92/B, H1151 Budapest, Hungary

[21] Appl. No.: 838,055
[22] Filed: Feb. 19, 1992

Related U.S. Application Data

[63] Continuation-in-part of PCT/HU90/00046, Jul. 6, 1990.

[30] Foreign Application Priority Data

Jul. 7, 1989 [HU] Hungary ............................. 3445/89

[51] Int. Cl.⁵ ................................................ A61F 9/06
[52] U.S. Cl. ....................................................... 2/8
[58] Field of Search ................... 2/8, 10, 424; 219/147

[56] References Cited

U.S. PATENT DOCUMENTS

| | | | |
|---|---|---|---|
| 2,569,715 | 10/1951 | Green | 2/8 |
| 2,784,410 | 3/1957 | Gentz | 2/8 |
| 3,339,207 | 9/1967 | Perry | 2/8 |
| 3,517,392 | 6/1970 | Hodge | 2/8 |
| 3,601,814 | 8/1971 | Manz | 2/8 |
| 3,775,774 | 12/1973 | Herman | 2/8 |
| 4,422,185 | 12/1983 | Cook | 2/8 |
| 4,694,507 | 9/1987 | Owen | 2/8 |

FOREIGN PATENT DOCUMENTS

| | | |
|---|---|---|
| 0123662 | 6/1987 | European Pat. Off. . |
| 1961674 | 8/1970 | Fed. Rep. of Germany . |

Primary Examiner—Peter Nerbun
Attorney, Agent, or Firm—Michael N. Meller

[57] ABSTRACT

The invention concerns a welder's shield, in particular for arc welding, provided with a tilting fixing strap fixed to the head and an eye-protecting insert arranged at the eye-level of the welder. The shield according to the invention can be characterized in that on the forepart of the welder's shield (1) there is an adjustable moving element actuated by the jaw of the welder; by the aid of the movable element (8) and the moving mechanism connected to the moving element (8) the vitreous part of the spectacles, namely the mirror-glass (6), can be displaced from its basic position, and beneath the mirror-glass (6) there is a flatglass (5) arranged being parallel with the plane of the mirror-glass (6) in the basic position.

9 Claims, 6 Drawing Sheets

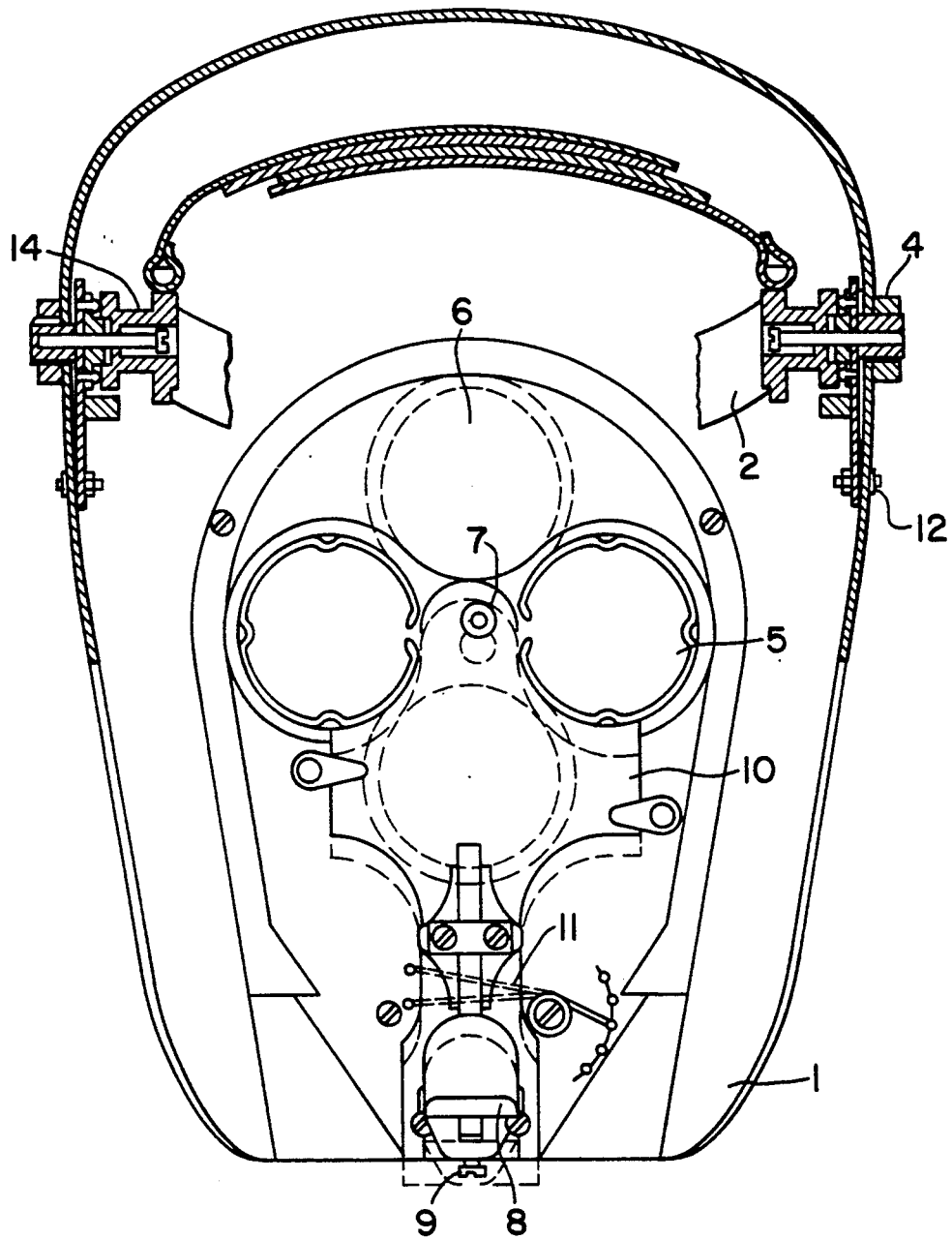
F I G. 2

WELDER'S SHIELD, IN PARTICULAR FOR ARC WELDING

This is a continuation-in-part of PCT application No. PCT/HU90/00046, filed Jul. 6, 1990.

TECHNICAL FIELD

The invention relates to a welder's shield, in particular to arc welding, provided with a tilting strap being fixed on the head and an eye-protecting insert arranged at eye-level of the welder.

BACKGROUND ART

In several fields of industry structural elements are formed, maintained and repaired by welding. The welding process itself is an operation causing numerous accidents. Welding can be performed only by using protective spectacles and a shield—a welder's shield—protecting the welder.

Generally, welder's shields are manufactured in uniform sizes and do not yield the necessary protection for the welder.

In the majority of cases welding can be performed while the welder is holding the shield with one hand. Thus welding can be performed only with the assistance of an auxiliary person if materials are to be welded which have to be fitted accurately to each other prior to welding.

Welder's shields are also known which can be fitted onto the welder's head, however, these do not meet requirements.

Common characteristics and drawbacks of known welder's shield lie in the fact that the eye-protecting layer arranged at the eye-level is essentially a mirror-glass which protects the eyes of the welder against beams and sparks occurring in the course of welding. However, it is unsuitable for slag removal, as the welded joint cannot be seen through such glass. As a consequence, slagging is often carried out without the welder wearing the protective spectacles resulting frequently in ocular lesion.

DISCLOSURE OF THE INVENTION

The aim of the present invention is to develop a welder's shield, by the aid of which deficiencies of known and applied shields can be eliminated and which is equally suitable for welding and slagging, while simultaneously both hands of the welder are free.

The invention is based on the recognition, that by building in two parallel glasses with different characteristics, such as a mirror-glass and a flatglass, as well as by actuating the mirror-glass from the inside of the welder's shield, preferably by means of the jaw of the welder, deficiencies of known solutions can be eliminated and a novel shield may be obtained fitting the head of the welding person.

The aim set for the invention is achieved by means of a welder's shield which is provided with a movable adjustable element to be actuated by the jaw of the welder and by the aid of a movable element and a moving mechanism connected to the movable element. The vitreous part of the spectacles—namely the mirror-glass—can be displaced from its basic position while beneath the mirror glass there is a flatglass arranged parallel with the plane of the mirror-glass in the basic position.

In a preferred embodiment of the invention the moving mechanism is essentially an eccentric device connected to the moving element actuated against a spring-force and rotating the mirror-glass about a stub axle, while it comprises two separate circular mirror-glass and flatglasses, respectively.

In another preferred embodiment of the invention the moving mechanism is a single-armed lever actuated by a rod connected to the moving element tilting the mirror-glass from its basic position, preferably it has a quadrangular i.e. rectangular mirror-glass.

In a further preferred embodiment of the welder's shield according to the invention the single-armed lever is assembled with a spring-box connected to the rod of the moving element, the load-arm being actuated by the spring in the spring-box and the ball- and socket being connected to the load-arm and tilting the mirror-glass.

In another embodiment of the welder's shield according to the invention the moving mechanism is assembled with a single armed lever connected to the moving element, actuated by the regulator on the outside free surface of the welder's shield, tilting the mirror-glass from its basic position and placed on the inside surface of the welder's shield where the regulator is assembled of a fixed base plate, a fastener fixed to the balance arm of the single-armed lever and provided with teeth inclined in the same direction as the outside base plate, a locking wedge getting wedged in between the teeth of the fastener in moving and provided with a catch fixing the regulator in a position, springs arranged preferably, a fastener releasing mechanism ceasing cam the fixed state, as well as a setting element defining the position of said mechanism.

Another preferred embodiment of the welder's shield according to the invention is provided with an adjustable fixing strap with arresting means, which is provided with hinges or springs.

With a further preferred embodiment of the welder's shield according to the invention the fixing strap is provided with an adhesive tearing-fastener and both the flatglass and the mirror-glass can be changed.

Two preferable embodiments of the invention will be detailed with reference to the enclosed drawings, wherein:

DESCRIPTION OF DRAWINGS

FIG. 2 is a section taken along the plane A—A of the embodiment according to FIG. 1.

Referring to the drawings, FIG. 1 shows the sectional side-view of a preferred embodiment of the welder's shield according to the invention.

BEST MODE OF CARRYING OUT THE INVENTION

Figure 1:
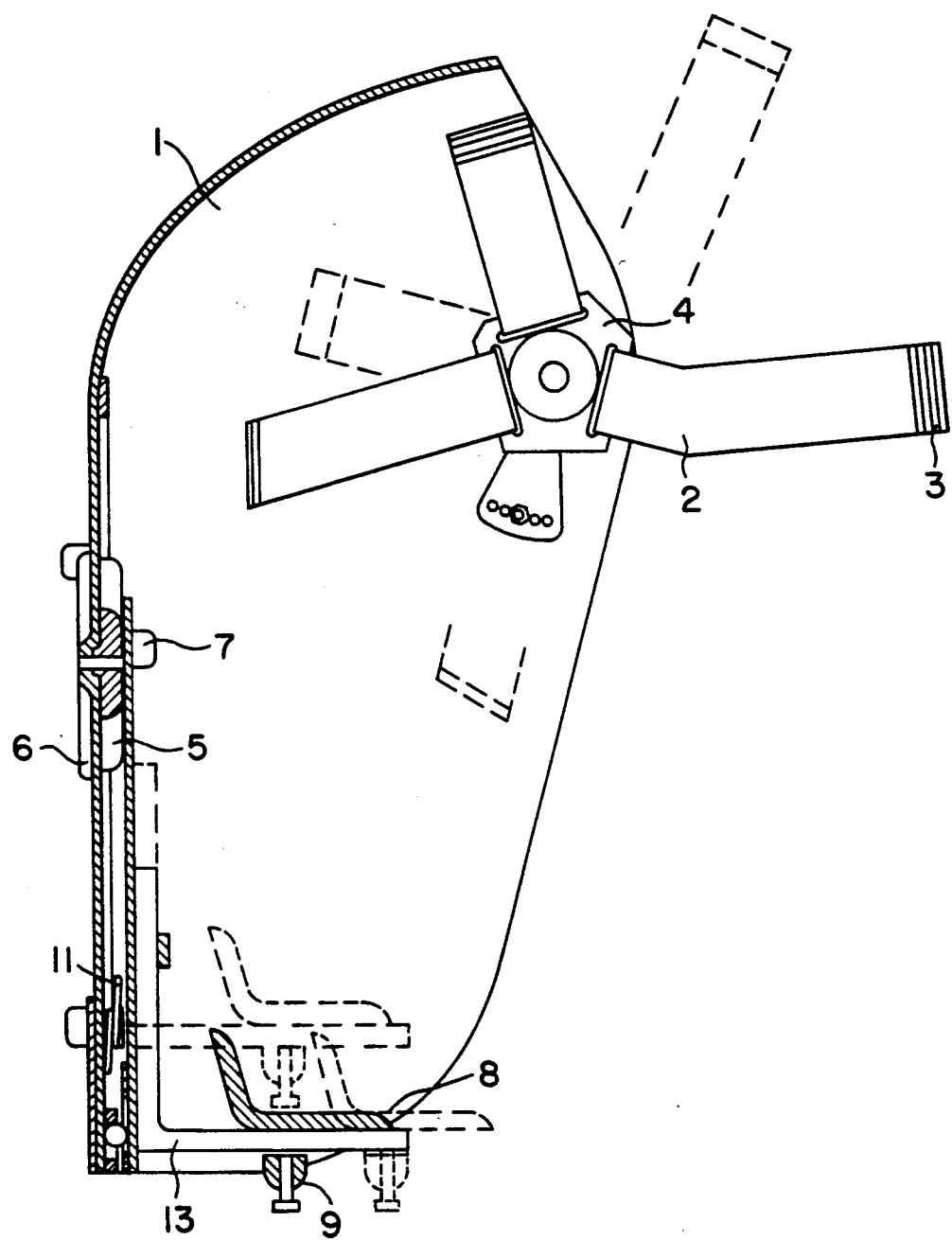
FIG. 1 is the side-view of an embodiment the Welder's shield according to the invention, partially in section.

The welder's shield 1 consists of a fixing strap 2 arranged on both sides of the welder's shield. The strap is attached to an arrester 4 as well as to the shield part protecting the face of the welding person. Adjustability of the fixing strap 2 is assured by the adhesive-tearing fasteners 3 formed on the strap-branches. As a consequence, the welder's shield can be accurately adjusted to the head-size of the welder. On the bottom part of the welder's shield 1 there is an adjustable moving element 8 fixed on a carrier 13, which can be brought into a desired position by means of a setting element 9. The moving element 8 is to be adjusted always so that it occupies accurately the position under the jaw of the welder. The moving element 8 is connected to a moving mechanism, which, as shown in FIG. 2, can move the protective spectacles into a desired position. That is a mirror-glass 6 can be arranged at the eye-level of the welder in front of a flatglass 5, parallel with the flatglass 5 in the basic position by rotation about a stub axle 7. Mirror-glass 6 and flat-glass 5 are formed of separate circular pairs of glass.

With this embodiment, the moving-rotating mechanism putting the mirror-glass 6 into motion consists essentially of an eccentric device 10 actuated by the moving element 8 against a spring 11. In FIG. 2 a dashed line shows the rotated position of the mirror-glass 6 away from the basic position.

From FIG. 2 the construction of the arrester 4 and arrangement thereof becomes obvious. That is the arrester is fixed to the side of the welder's shield 1 by means of fixing means 12 and can be provided with a hinge or a spring.

Operation of the welder's shield as illustrated in FIGS. 1 and 2 will be detailed below.

First of all, before beginning the welder controls the shield 1 and adjusts it to his head. Thus, the moving element 8 is set according to the head-size, fixing straps 2 are also adjusted. Thereafter, the shield is put onto the welder's head.

In the basic position the mirror-glass 6 and the flat-glass 5 are arranged parallel to each other and cover one another. In this position the welder's shield 1 is in its working position and welding can be performed. Frequently, however, the necessity arises, that the welder must see the workpiece to be welded accurately, or the welded joint just having prepared by interrupting the welding process. In this case the mirror-glass 6 interferes with free sight.

Now, the welder wearing the shield 1 actuates with his jaw the moving element 8 and thus the mechanism moving the mirror-glass 6. That is the welder pushes the moving element 8 downwardly with his jaw thereby against the spring the eccentric device 10 is put into motion. As a consequence, the mirror-glass 6 is rotated about the stubaxle 7 to the position shown in FIG. 2 so the workpiece becomes absolutely visible for the welder through the flatglass 5. The welded joint just having been finished can be seen as well. As soon as the pressure exerted by the jaw ceases, the moving element 8 returns to its basic position, so the spring-force also ceases. Accordingly the eccentric device 10 and the mirror-glass 6 return to their starting position.

The operation can be optionally repeated during the course of the welding process, so the welder will be able to control his work continuously without taking down the shield or using his free hand for taking down the shield. In such manner, if a larger surface is to be covered with a larger arc, the welder can use both hands. He is able to hold the electrode for proceeding with the operation and auxiliary personnel are unnecessary, so accidents can be eliminated too.

If the flatglass 5 is lies at eye-level, removal of slag can be performed easily, the welder is not afraid of ocular lesion, as hot slag does not cause ocular lesion.

Fixing strap 2 is adjustable and is arranged diagonally in direction of the welders ears. Built-in arrester 4 promotes easy manipulation, as after having tilted-up the shield 1, it can be fixed in the desired position on the head, so it is not necessary to take it down between two working phases.

Figure 3:
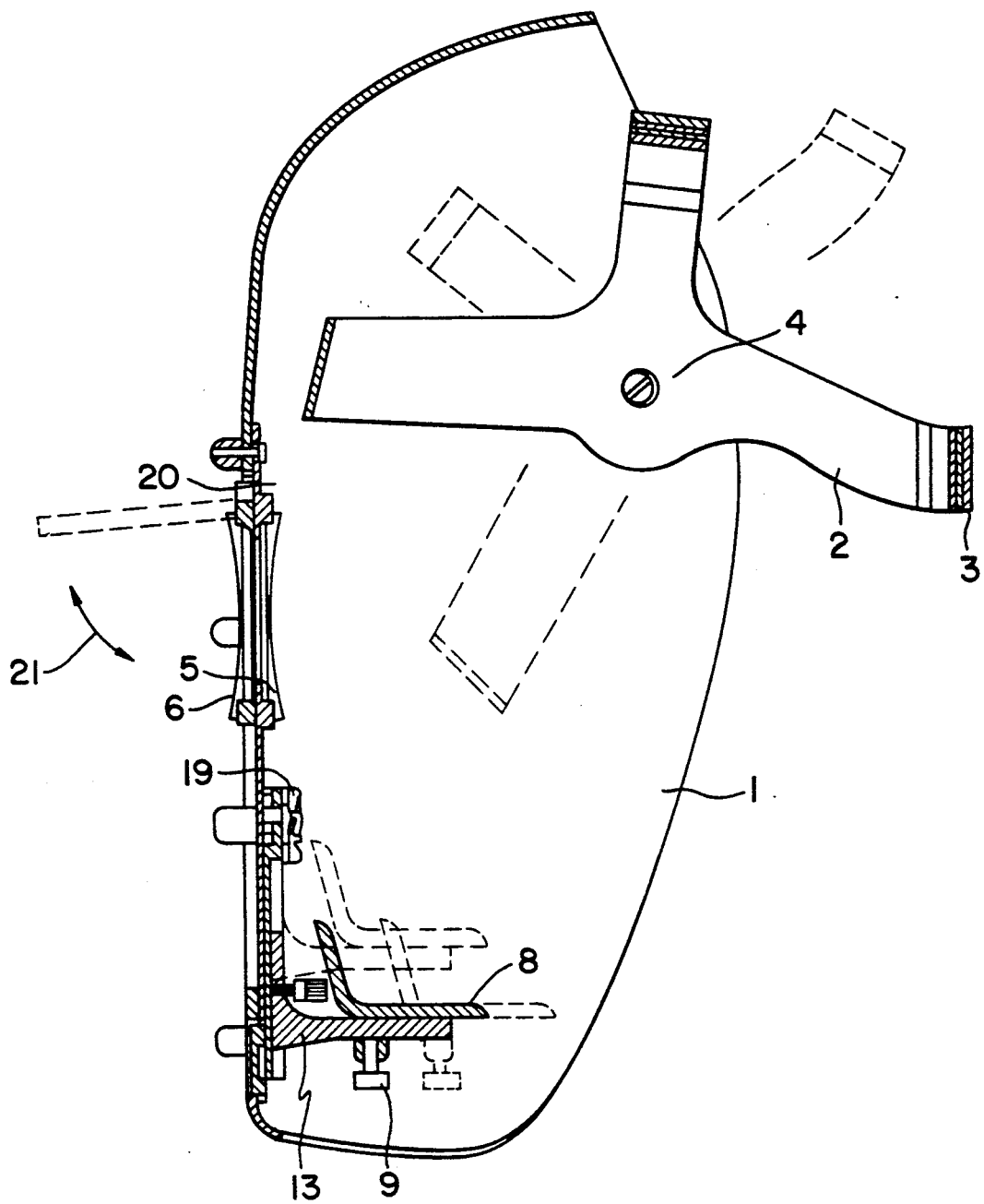
FIG. 3 is a sectional-side-view of another embodiment of the invention.

FIG. 3 illustrates another embodiment of the welder's shield shown in sectional side-view. With this embodiment both the flatglass 5 and the mirror-glass 6 are shaped from a quadrangular, preferably rectangular glass-plate. Layout of the welder's shield corresponds essentially to the layout of the shield as described in connection with the embodiment according to FIG. 1, the difference lies merely in the shape of the mirror-glass 6, and the flatglass 5, as well as in formation of the moving mechanism connected to the moving element 8 for putting the mirror-glass 6 into motion. As a consequence, the condition of motion for the mirror-glass 6 will also change.

Figure 4:
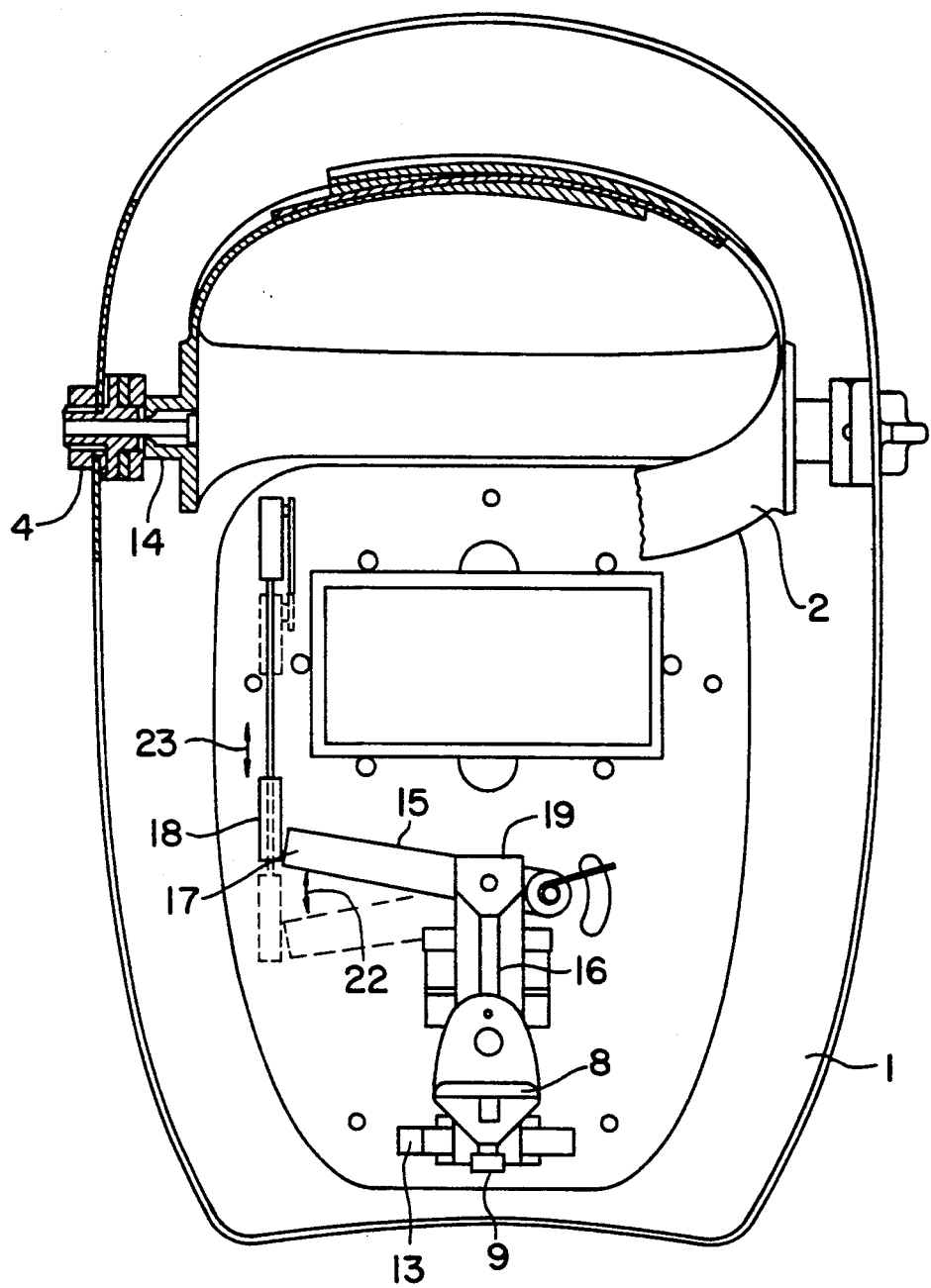
FIG. 4 is a rear view of the welder's shield according to the invention.

Referring to FIGS. 3 and 4, in this embodiment the moving mechanism is assembled from a rod 16 connected to the moving element 8, of a spring-box 19 connected to the end of the rod 16 lying opposite to the moving element 8, as well as from the arm of a ball- and socket 18 adapted to be actuated by a load-arm 17 connected to the spring-box 19 and tilting the mirror-glass 6 from its basic position. (See FIG. 4.)

Mode of operation of the welder's shield, as illustrated in FIGS. 3 and 4 will be detailed, as follows:

Prior to beginning welding, the welder performs adjustments, as described in connection with FIG. 1. Thereafter he puts the shield of his head. Prior to beginning work the shield is not lying in front of his face, however, it occupies a position at an angle of 85°-90° in front of the face by virtue of the arrester 4.

Prior to begin welding, the shield is turned in front of face so that both glasses, namely the mirror-glass 6 and the flat-glass 5 are lying at eye-level and occupy their basic position.

When it becomes necessary to examine the weld joint, the moving element 8 is pushed with the jaw. Therefore, the moving element 8 moves the rod 16, said rod is connected to the load-arm 17 via the springbox 19. After having pressed the moving element 8 down, the load-arm 17 moves in the downward direction of the arrow 22 indicated with a discontinuous line in FIG. 4. At the same time the load-arm 17 moving downwards carries with it the ball- and sockets 18 in direction of the arrow 23 downwards, which displaces the mirror-glass 6 upwards, in direction of the arrow 21, as illustrated in FIG. 3. As a consequence, the weld joint may be examined through the flatglass 5, in case of necessity slagging can be performed.

When the force effect affecting the moving element 8 ceases, the spring in the spring-box 19 returns the load-arm 17 and therewith the arm of the ball- and sockets 18 to the original respective starting position, thereby the mirror-glass 6 occupies its basic position.

This proceedings can be optionally repeated, as necessary.

With the preferred embodiments shown in former figures during welding the mechanism moving the glasses for protection of the eyes is placed inside the welder's shield. However, the moving elements may fail e.g. the spring may break down, which is very dangerous, because a piece broken from the spring can injure the eyes of the wearer.

Figure 5:
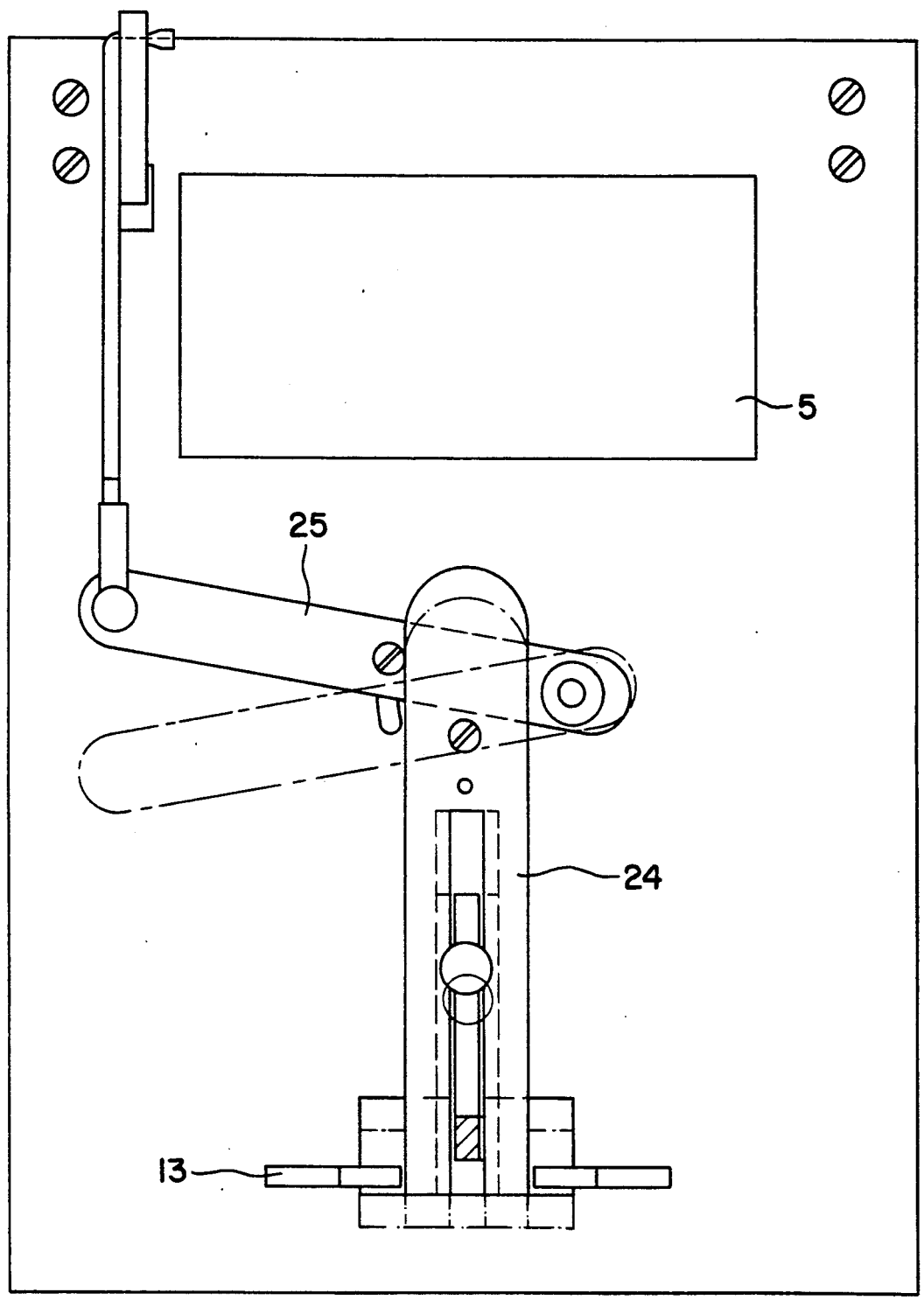
FIG. 5 is a rear view of the portion A of a further embodiment of the welder's shield according to the invention shown in FIG. 4.
Figure 6:
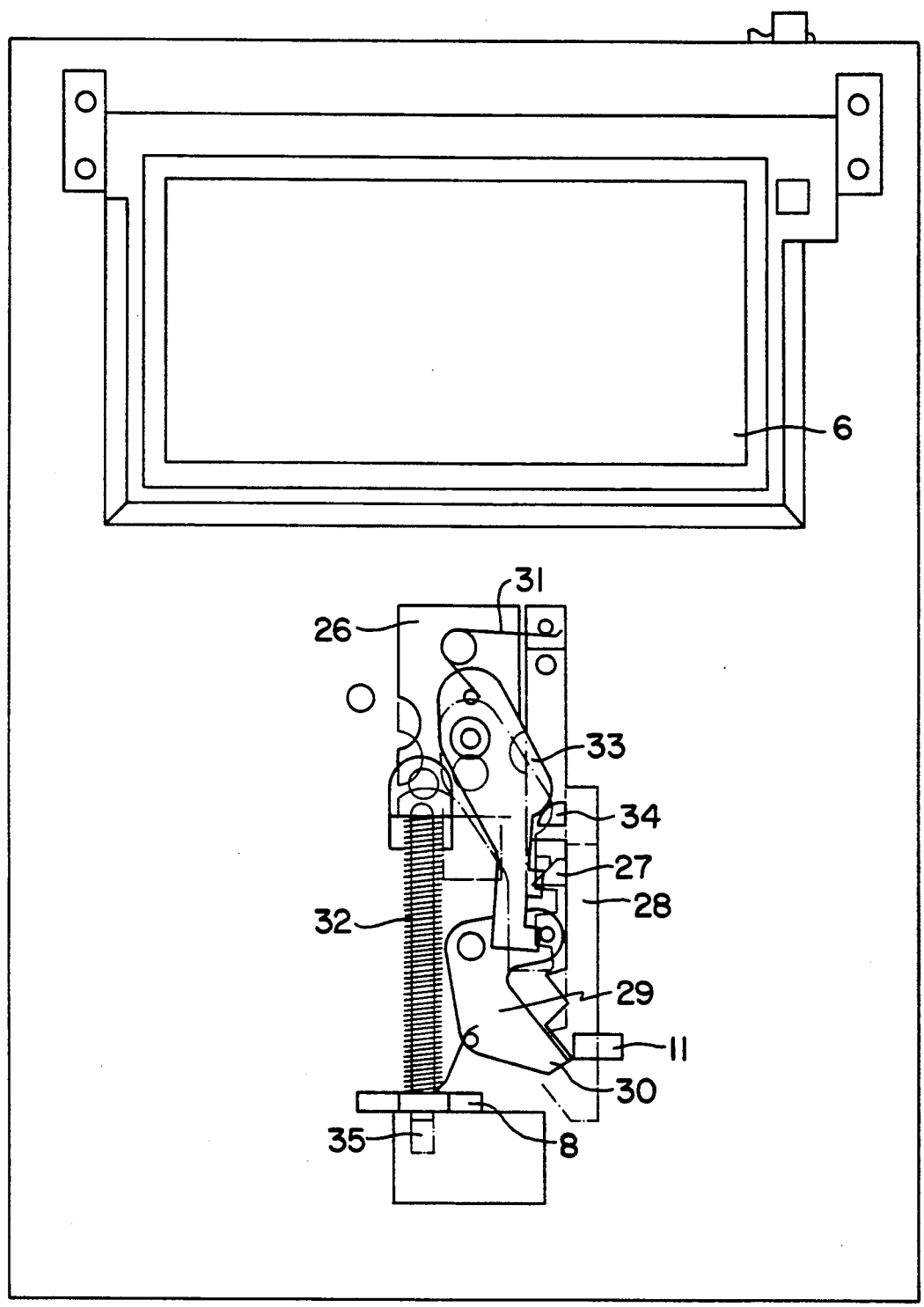
FIG. 6 is a partial front-view of the welder's shield shown in FIG. 5.

Experiences gained by experiments lead to the formation of the moving mechanism shown in FIGS. 5 and 6. Since there is no significant change in the formation of the welder's shield compared to the solution according to the FIGS. 3 and 4, only the moving mechanism, i.e. its part A shown in FIG. 4 is represented in FIGS. 5 and 6.

The difference between the solution specified above and the solution according to the invention of FIGS. 5 and 6 lies in that a regulator 24 containing the moving elements tilting the mirror-glass is placed on the outside free surface of the welder's shield. The moving element 8, is formed by a single-armed lever 25 inside the welder's shield. (See FIG. 5).

In FIG. 6 the formation of the moving mechanism is shown. The moving mechanism is actuated by the regulator 24, said regulator 24 is essentially assembled of a fixed outside base plate 26, a fastener 28 provided with teeth 27 inclined in the same direction as the base plate 26, a locking wedge 29 adapted to be wedged between the teeth 27 of the fastener 28 when tilting the mirror-glass and provided with an end piece 30 fixing the control mechanism 24 in a desired position. Springs 31 and 32 are provided to arrange a fastener releasing mechanism 33 in a preferable position when it leaves its fixed state and a setting element 34 further defines the position of said mechanism 33.

The regulator 24 moves along an imaginary symmetry axis of the welder's shield.

When the moving element 8 is pressed downwardly the outside base plate 26 moves in the same direction as the regulator 24. Also, when the moving element 8 is pressed downwardly the fastener 28 provided with teeth 27 inclined in the same direction as the base plate 26, fixed to the balance arm of the single-armed lever 25 also moves but it must move farther than the regulator 24.

When the regulator 24 is completely pressed down, the closing wedge 29 gets wedged between the teeth 27 of the fastener 28 by the action of the springs 31 and 32.

As a result of the interrelated motions specified above the mirror-glass 6 remains in its top dead center position by means of the gear specified above while the springs 31 and 32 exert an adequate stretching force to the closing wedge 29.

The regulator 24 is formed in such a manner that the base plate 26 and the fastener releasing mechanism 33 fixed to the outside base plate 26 moves along a longer path than the fastener 28 fixed to the balance arm of the single-armed lever 25 and provided with teeth 27. The difference between these two paths is enough to actuate the fastener releasing mechanism 33 in an alternating way.

The position of the fastener releasing mechanism 33 is defined by the setting element 34, formed as a cam, as well as the stretching force of the springs 31 and 32.

When the regulator 24 is pressed down again the closing wedge 29 is removed from the teeth 27 of the fastener 28 and the mirror-glass 6 and the control mechanism 24 more into their static condition by means of the springs 31 and 32.

Such formation of moving mechanism eases the work of the welder, because he need not continue to hold the moving element 8 with his jaw and the position of the mirror-glass 6 facilitate safer processing.

The advantage of the welder's shield according to the invention lies in the simplicity of actuating by means of his jaw the welder can always assure free sight without taking down the shield.

A further advantage lies in that by using the shield according to the invention both hands are free and both hands can be used for the welding process, as holding of the shield becomes superfluous.

As a further advantage it should be mentioned that it can be optionally adjusted, brought into compliance with the head-size of the welder. By virtue of the arrangement of the two glasses, namely the mirror-glass and the flat-glass, slagging can be performed without removing the shield from in front of the face, in such a manner ocular lesions resulting frequently from slagging can be carefully eliminated.

We claim:

1. Welding shield in particular for arc welding provided with an adjustable fixing strap adapted to be placed onto the head of a welder, said shield having an inner surface adapted to face said welder and a lookout made of mirror-glass provided with an insert protecting the eye of the welder, said mirror-glass being arranged in a basic position at the eye-level of the welder when wearing said shield, in said basic position said mirror-glass is arranged parallel and adjacent a transparent flat-glass; a moving mechanism for moving said mirror-glass from its basic position to a second position away from said flat glass, said moving mechanism including a single-arm lever arranged on an inner surface of said welding shield, said lever being actuated by the chin of the welder, said moving mechanism being connected to a control mechanism having a base-plate fixed to a surface of said shield, a fastener arranged on a surface of said base-plate, having teeth, facing said welding shield and fixed to the arm of said single-arm lever, a closing wedge adapted to mesh with said teeth of said fastener for fixedly mounting said control mechanism in a given position, spring members for urging said control mechanism away from said given position and a control element adapted to release said control mechanism from said given position, said fastener, said closing wedge and said spring members being mounted on an outer surface of said shield opposite to said inner surface of said shield.

2. Welding shield as claimed in claim 1 wherein said control element is formed as a cam.

3. Welding shield as claimed in claim 1 wherein said mirror-glass is square- or oblong-shaped.

4. Welding shield as claimed in claim 2 wherein said mirror-glass is square- or oblong-shaped.

5. Welding shield as claimed in claim 1, wherein said moving mechanism includes a rod and a ball and socket joint and said single arm lever comprises a spring-box connected to said rod of the moving mechanism, said ball-and socket joint being actuated by a spring encased in said spring-box for tilting said mirror-glass to and away from said basic position.

6. Welding shield as claimed in claim 1, wherein said moving mechanism is an eccentric device connected to a moving element actuated against a spring and rotating said mirror-glass and flat-glass about the axis of a swivel pin and wherein said mirror-glass and flat-glass are separately formed circular glasses.

7. Welding shield as claimed in claim 1, wherein both said mirror-glass and flat-glass are exchangeable.

8. Welding shield as claimed in claim 6 wherein said control element is formed as a cam.

9. Welding shield as claimed in claim 6 wherein said mirror-glass square- or oblong-shaped.

* * * * *